(12) United States Patent  
Rosinko et al.

(10) Patent No.: US 9,173,998 B2  
(45) Date of Patent: Nov. 3, 2015

(54) SYSTEM AND METHOD FOR DETECTING OCCLUSIONS IN AN INFUSION PUMP

(71) Applicant: Tandem Diabetes Care, Inc., San Diego, CA (US)

(72) Inventors: Mike Rosinko, Anaheim, CA (US); Geoffrey Kruse, San Diego, CA (US); Paul Harris, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 344 days.

(21) Appl. No.: 13/829,115

(22) Filed: Mar. 14, 2013

(65) Prior Publication Data

US 2014/0276409 A1    Sep. 18, 2014

(51) Int. Cl.  
*A61M 5/168* (2006.01)  
*A61M 5/142* (2006.01)

(52) U.S. Cl.  
CPC ....... *A61M 5/16831* (2013.01); *A61M 5/14216* (2013.01); *A61M 5/14244* (2013.01); *A61M 2005/14268* (2013.01); *A61M 2005/16863* (2013.01); *A61M 2205/3331* (2013.01); *A61M 2205/3368* (2013.01)

(58) Field of Classification Search  
CPC ..................... A61M 5/16831; A61M 5/16854; A61M 5/16859  
See application file for complete search history.

(56) References Cited

U.S. PATENT DOCUMENTS

| | | | |
|---|---|---|---|
| 3,985,133 A | 10/1976 | Jenkins et al. | |
| 4,178,938 A | 12/1979 | Au | |
| 4,650,471 A | 3/1987 | Tamari | |
| 4,919,596 A | 4/1990 | Slate et al. | |
| 5,000,739 A | 3/1991 | Kulisz et al. | |
| 5,085,644 A | 2/1992 | Watson et al. | |
| 5,087,245 A | 2/1992 | Doan | |
| 5,103,211 A | 4/1992 | Daoud et al. | |

(Continued)

FOREIGN PATENT DOCUMENTS

| | | |
|---|---|---|
| WO | WO9532013 A1 | 11/1995 |
| WO | WO0130422 A1 | 5/2001 |

(Continued)

OTHER PUBLICATIONS

PCT Search Report and Written Opinion dated Jun. 9, 2014 for PCT Application No. PCT/2014/018861 filed Feb. 27, 2014, 10 pages.

(Continued)

*Primary Examiner* — Nicholas Lucchesi  
*Assistant Examiner* — Melissa A Snyder  
(74) *Attorney, Agent, or Firm* — Patterson Thuente Pedersen, P.A.

(57) ABSTRACT

Occlusions in a delivery line of an infusion pump can be detected by measuring pressure differentials in the pump over short periods of time in order to minimize the effects of long term systematic sensor changes. In a delivery mode such as basal insulin delivery where a small portion of a volume of fluid is delivered, pressure readings can be obtained before and after the motor move to deliver each portion and compared. The differentials after one or more motor moves can be compared to determine whether an occlusion is present. In a delivery mode such as bolus insulin delivery in which an entire volume of fluid is delivered, pressure differentials can be obtained for consecutive deliveries at a common point in the delivery cycle of each delivery. Comparison of these pressure values can be used to determine whether an occlusion is present.

18 Claims, 14 Drawing Sheets

(56) References Cited

U.S. PATENT DOCUMENTS

| | | |
|---|---|---|
| 5,131,816 A | 7/1992 | Brown et al. |
| 5,178,603 A | 1/1993 | Prince |
| 5,215,450 A | 6/1993 | Tamari |
| 5,242,408 A | 9/1993 | Jhuboo et al. |
| 5,247,434 A | 9/1993 | Peterson et al. |
| 5,273,406 A | 12/1993 | Feygin |
| 5,304,126 A | 4/1994 | Epstein et al. |
| 5,342,180 A | 8/1994 | Daoud |
| 5,423,743 A | 6/1995 | Butterfield |
| 5,429,483 A | 7/1995 | Tamari |
| 5,438,510 A | 8/1995 | Bryant et al. |
| 5,464,392 A | 11/1995 | Epstein et al. |
| 5,482,446 A | 1/1996 | Williamson et al. |
| 5,498,421 A | 3/1996 | Grinstaff et al. |
| 5,551,850 A | 9/1996 | Williamson et al. |
| 5,584,667 A | 12/1996 | Davis |
| 5,634,896 A | 6/1997 | Bryant et al. |
| 5,639,473 A | 6/1997 | Grinstaff et al. |
| 5,658,252 A | 8/1997 | Johnson |
| 5,695,473 A | 12/1997 | Olsen |
| 5,800,387 A | 9/1998 | Duffy et al. |
| 5,803,917 A | 9/1998 | Butterfield et al. |
| 5,885,614 A | 3/1999 | Hirsch |
| 5,935,106 A | 8/1999 | Olsen |
| 5,971,722 A | 10/1999 | Maget et al. |
| RE36,871 E | 9/2000 | Epstein et al. |
| 6,120,460 A | 9/2000 | Abreu |
| 6,158,965 A | 12/2000 | Butterfield et al. |
| 6,210,361 B1 | 4/2001 | Kamen et al. |
| 6,280,408 B1 | 8/2001 | Sipin |
| 6,302,653 B1 | 10/2001 | Bryant et al. |
| 6,310,270 B1 | 10/2001 | Huang et al. |
| 6,358,225 B1 | 3/2002 | Butterfield |
| 6,371,732 B1 | 4/2002 | Moubayed et al. |
| 6,381,493 B1 | 4/2002 | Stadler et al. |
| 6,382,923 B1 | 5/2002 | Gray |
| 6,398,760 B1 | 6/2002 | Danby |
| 6,416,291 B1 | 7/2002 | Butterfield et al. |
| 6,416,293 B1 | 7/2002 | Bouchard et al. |
| 6,447,443 B1 | 9/2002 | Keogh et al. |
| 6,447,522 B2 | 9/2002 | Gambale et al. |
| 6,464,667 B1 | 10/2002 | Kamen et al. |
| 6,471,689 B1 | 10/2002 | Joseph et al. |
| 6,475,180 B2 | 11/2002 | Peterson et al. |
| 6,485,263 B1 | 11/2002 | Bryant et al. |
| 6,485,461 B1 | 11/2002 | Mason et al. |
| 6,537,268 B1 | 3/2003 | Gibson et al. |
| 6,604,908 B1 | 8/2003 | Bryant et al. |
| 6,663,359 B2 | 12/2003 | Gray |
| 6,669,669 B2 | 12/2003 | Flaherty et al. |
| 6,740,059 B2 | 5/2004 | Flaherty |
| 6,749,403 B2 | 6/2004 | Bryant et al. |
| 6,759,386 B2 | 7/2004 | Franco |
| 6,801,420 B2 | 10/2004 | Talbot et al. |
| 6,804,002 B2 | 10/2004 | Fine et al. |
| 6,877,713 B1 | 4/2005 | Gray et al. |
| 6,905,479 B1 | 6/2005 | Bouchard et al. |
| 6,948,918 B2 | 9/2005 | Hansen |
| 6,997,202 B2 | 2/2006 | Olander |
| 7,011,682 B2 | 3/2006 | Lashinski et al. |
| 7,029,455 B2 | 4/2006 | Flaherty |
| 7,090,648 B2 | 8/2006 | Sackner et al. |
| 7,091,179 B2 | 8/2006 | Franco |
| 7,107,706 B1 | 9/2006 | Bailey, Sr. et al. |
| 7,137,964 B2 | 11/2006 | Flaherty |
| 7,150,737 B2 | 12/2006 | Purdy et al. |
| 7,153,823 B2 | 12/2006 | Franco |
| 7,163,520 B2 | 1/2007 | Bernard et al. |
| 7,166,280 B2 | 1/2007 | Franco |
| 7,187,528 B2 | 3/2007 | Talbot et al. |
| 7,193,521 B2 | 3/2007 | Moberg et al. |
| 7,264,730 B2 | 9/2007 | Connell et al. |
| 7,265,091 B2 | 9/2007 | Lue et al. |
| 7,303,680 B2 | 12/2007 | Connell et al. |
| 7,318,892 B2 | 1/2008 | Connell et al. |
| 7,338,464 B2 | 3/2008 | Blischak et al. |
| 7,351,340 B2 | 4/2008 | Connell et al. |
| 7,429,269 B2 | 9/2008 | Schwammenthal et al. |
| 7,460,350 B2 | 12/2008 | Talbot et al. |
| 7,473,239 B2 | 1/2009 | Wang et al. |
| 7,476,209 B2 | 1/2009 | Gara et al. |
| 7,503,903 B2 | 3/2009 | Carlisle et al. |
| 7,507,235 B2 | 3/2009 | Keogh et al. |
| 7,514,401 B2 | 4/2009 | Franco |
| 7,517,440 B2 | 4/2009 | Anex et al. |
| 7,534,226 B2 | 5/2009 | Mernoe et al. |
| 7,559,524 B2 | 7/2009 | Gray et al. |
| 7,604,592 B2 | 10/2009 | Freeman et al. |
| 7,621,893 B2 | 11/2009 | Moberg et al. |
| 7,654,127 B2 | 2/2010 | Krulevitch et al. |
| 7,704,227 B2 | 4/2010 | Moberg et al. |
| 7,766,301 B2 | 8/2010 | Gray et al. |
| 7,766,873 B2 | 8/2010 | Moberg et al. |
| 7,775,975 B2 | 8/2010 | Brister et al. |
| 7,776,006 B2 | 8/2010 | Childers et al. |
| 7,811,279 B2 | 10/2010 | John |
| 7,892,206 B2 | 2/2011 | Moberg et al. |
| 7,922,462 B2 | 4/2011 | Preuthun et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,944,366 B2 | 5/2011 | Krulevitch et al. |
| 7,955,295 B2 | 6/2011 | Lee et al. |
| 7,959,608 B2 | 6/2011 | Nash et al. |
| 7,963,945 B2 | 6/2011 | Miller et al. |
| 7,967,022 B2 | 6/2011 | Grant et al. |
| 7,998,111 B2 | 8/2011 | Moberg et al. |
| 8,002,747 B2 | 8/2011 | Lord et al. |
| 8,007,460 B2 | 8/2011 | Gelfand et al. |
| 8,012,121 B2 | 9/2011 | Goodson et al. |
| 8,032,226 B2 | 10/2011 | Miller et al. |
| 8,034,026 B2 | 10/2011 | Grant et al. |
| 8,062,257 B2 | 11/2011 | Moberg et al. |
| 8,065,096 B2 | 11/2011 | Moberg et al. |
| 8,100,852 B2 | 1/2012 | Moberg et al. |
| 8,105,265 B2 | 1/2012 | Demers et al. |
| 8,109,906 B2 | 2/2012 | Smisson et al. |
| 8,114,350 B1 | 2/2012 | Silver et al. |
| 8,147,511 B2 | 4/2012 | Perry et al. |
| 8,182,447 B2 | 5/2012 | Moberg et al. |
| 8,211,093 B2 | 7/2012 | Miller et al. |
| 8,223,028 B2 | 7/2012 | Mandro et al. |
| 8,267,893 B2 | 9/2012 | Moberg et al. |
| 8,282,601 B2 | 10/2012 | Mernoe et al. |
| 8,287,495 B2 | 10/2012 | Michaud et al. |
| 8,287,514 B2 | 10/2012 | Miller et al. |
| 8,298,183 B2 | 10/2012 | Menot et al. |
| 8,298,184 B2 | 10/2012 | Diperna et al. |
| 8,323,188 B2 | 12/2012 | Tran |
| 8,414,532 B2 | 4/2013 | Brandt et al. |
| 8,414,563 B2 | 4/2013 | Kamen et al. |
| 8,608,699 B2 | 12/2013 | Blomquist |
| 8,694,331 B2 | 4/2014 | DeBelser et al. |
| 2002/0040208 A1 | 4/2002 | Flaherty et al. |
| 2002/0072733 A1 | 6/2002 | Flaherty |
| 2003/0097082 A1 | 5/2003 | Purdy et al. |
| 2004/0133166 A1 | 7/2004 | Moberg et al. |
| 2004/0133220 A1 | 7/2004 | Lashinski et al. |
| 2004/0138744 A1 | 7/2004 | Lashinski et al. |
| 2004/0153146 A1 | 8/2004 | Lashinski et al. |
| 2004/0260233 A1 | 12/2004 | Garibotto et al. |
| 2005/0054994 A1 | 3/2005 | Cioanta et al. |
| 2005/0060030 A1 | 3/2005 | Lashinski et al. |
| 2005/0171512 A1 | 8/2005 | Flaherty |
| 2005/0171569 A1 | 8/2005 | Girard et al. |
| 2006/0116757 A1 | 6/2006 | Lashinski et al. |
| 2006/0264835 A1 | 11/2006 | Nielsen et al. |
| 2007/0100222 A1 | 5/2007 | Mastrototaro et al. |
| 2007/0112301 A1 | 5/2007 | Preuthun et al. |
| 2007/0149926 A1 | 6/2007 | Moberg et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |

(56) References Cited

U.S. PATENT DOCUMENTS

| | | |
|---|---|---|
| 2008/0058697 A1 | 3/2008 | Kamen et al. |
| 2008/0082040 A1 | 4/2008 | Kubler et al. |
| 2008/0125700 A1 | 5/2008 | Moberg et al. |
| 2008/0172027 A1 | 7/2008 | Blomquist |
| 2008/0221523 A1 | 9/2008 | Moberg et al. |
| 2009/0067989 A1 | 3/2009 | Estes et al. |
| 2009/0069746 A1 | 3/2009 | Miller et al. |
| 2009/0069749 A1 | 3/2009 | Miller et al. |
| 2009/0069785 A1 | 3/2009 | Miller et al. |
| 2010/0037680 A1 | 2/2010 | Moberg et al. |
| 2010/0185142 A1 | 7/2010 | Kamen et al. |
| 2010/0185175 A1 | 7/2010 | Kamen et al. |
| 2010/0198183 A1 | 8/2010 | Lanigan et al. |
| 2010/0217192 A1 | 8/2010 | Moberg et al. |
| 2010/0217193 A1 | 8/2010 | Moberg et al. |
| 2010/0218586 A1 | 9/2010 | Rosinko et al. |
| 2010/0262078 A1 | 10/2010 | Blomquist |
| 2011/0054397 A1 | 3/2011 | Menot et al. |
| 2011/0071465 A1 | 3/2011 | Wang et al. |
| 2011/0092894 A1 | 4/2011 | Mcgill et al. |
| 2011/0105877 A1 | 5/2011 | Wilt et al. |
| 2011/0125085 A1 | 5/2011 | Mcgill et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160650 A1 | 6/2011 | Chong et al. |
| 2011/0160654 A1 | 6/2011 | Hanson et al. |
| 2011/0166544 A1 | 7/2011 | Verhoef et al. |
| 2011/0190694 A1 | 8/2011 | Lanier, Jr. et al. |
| 2011/0208123 A1 | 8/2011 | Gray et al. |
| 2011/0230825 A1 | 9/2011 | Kamen et al. |
| 2012/0029433 A1 | 2/2012 | Michaud et al. |
| 2012/0029468 A1 * | 2/2012 | Diperna et al. ............. 604/500 |
| 2012/0029708 A1 | 2/2012 | Miller et al. |
| 2012/0030610 A1 | 2/2012 | Diperna et al. |
| 2013/0012917 A1 | 1/2013 | Miller et al. |
| 2014/0039392 A1 | 2/2014 | Geipel et al. |
| 2014/0054883 A1 | 2/2014 | Lanigan et al. |
| 2014/0276537 A1 | 9/2014 | Kruse |

FOREIGN PATENT DOCUMENTS

| | | |
|---|---|---|
| WO | WO2005082450 A1 | 9/2005 |
| WO | WO2007065944 A1 | 6/2007 |

OTHER PUBLICATIONS

U.S. Appl. No. 13/832,531, filed Mar. 15, 2013 inventor Kruse.
US 8,333,733, 12/2012, Lanigan et al. (withdrawn)

* cited by examiner

SYSTEM AND METHOD FOR DETECTING OCCLUSIONS IN AN INFUSION PUMP

FIELD OF THE INVENTION

The present invention relates to detecting occlusions in infusion pumps and, more particularly, the present invention relates to detecting occlusions in ambulatory infusion pumps that utilize replaceable fluid cartridges.

BACKGROUND

There are many applications in academic, industrial, and medical fields, as well as others, that can benefit from devices and methods capable of accurately and controllably delivering fluids, including liquids and gases, and that benefit from administering fluids in known and controlled quantities. Such devices and methods may be particularly useful in the medical field where many treatments include the administration of a known amount of a substance at predetermined intervals.

Insulin-injecting pumps have been developed for the administration of insulin for those suffering from both Type I and Type II diabetes. Recently, continuous subcutaneous insulin injection and/or infusion therapy with portable infusion devices has been adapted for the treatment of diabetes. Such therapy may include the regular and/or continuous injection or infusion of insulin into the skin of a person suffering from diabetes, and offers an alternative to multiple daily injections of insulin by an insulin syringe or an insulin pen. Such pumps can be ambulatory/portable infusion pumps that are worn by the user and that may use replaceable cartridges. Examples of such pumps and various features that can be associated with such pumps include those disclosed in U.S. patent application Ser. Nos. 13/557,163, 12/714,299, 12/538,018, U.S. Provisional Patent Application No. 61/655,883, U.S. Provisional Patent Application No. 61/656,967 and U.S. Pat. No. 8,287,495, each of which is incorporated herein by reference.

There are, however, some drawbacks associated with the use of subcutaneous injection syringes and/or some currently available infusion pumps for the delivery of insulin and other fluids. Infusion pumps generally deliver fluids to patients through a flexible line having a lumen through which the fluid is pumped from the device to the patient. These fluid lines can become occluded such that fluid cannot be pumped through the line to the patient. Early detection of an occlusion condition is important because the patient may not be receiving the prescribed amount of fluid, which can be harmful and in some instances even fatal. Although there are a number of systems that address the occlusion issue by incorporating sensors to sense whether pressure has increased in the fluid line, such systems can suffer from drawbacks related to accuracy, and from the cost associated with the use of sensors in disposable cartridges. For example, when measuring small signals over long periods of time, sensor drift or other long term systematic effects, such as temperature or ambient pressure changes, can affect the accuracy of the readings taken with such sensors.

There is an ongoing need for improvement in systems and methods for detecting occlusions in ambulatory infusion pumps.

SUMMARY OF THE INVENTION

Occlusions in a delivery line of an infusion pump can be detected by measuring pressure differentials in the pump over short periods of time in order to minimize the effects of long term systematic sensor changes. In a delivery mode such as basal insulin delivery where a small portion of a volume of fluid is delivered, pressure readings can be obtained before and after the motor move to deliver each portion and compared. The differentials after one or more motor moves can be compared to determine whether an occlusion is present. In a delivery mode such as bolus insulin delivery in which an entire volume of fluid is delivered, pressure differentials can be obtained for consecutive deliveries at a common point in the delivery cycle of each delivery. Comparison of these pressure values can be used to determine whether an occlusion is present.

In some embodiments, an ambulatory infusion system includes a disposable infusion cartridge having a collapsible reservoir for containing a fluid and an interior volume between an outer surface of the collapsible reservoir and an inner surface of a rigid shell disposed over the reservoir. A pump device can selectively receive the infusion cartridge and cooperate with the infusion cartridge to deliver fluid from the reservoir to the patient. A pressure sensor located in one of the infusion cartridge and the pump can obtain pressure readings in the interior volume of the cartridge. A processor can compare one or more pressure readings taken before, during or after operation of the pump and compare the readings to determine whether an occlusion is present.

In one embodiment, occlusions are detected while an ambulatory infusion pump is operating in a basal delivery mode. A pump motor is actuate to deliver a portion of fluid contained in a collapsible volume of the cartridge. A first pressure reading is obtained prior to actuating the motor and a second reading is obtained after actuating the motor. The pressure readings are compared and if the readings are not the same, or within a predetermined threshold of each other, an occlusion alarm is generated. In some embodiments, more than two pressure readings are compared.

In another embodiment, occlusions are detected while an ambulatory infusion pump is operated in a bolus delivery mode. In bolus delivery, the pump motor is actuated to deliver the entire contents of the collapsible volume. A pressure reading is obtained at a time prior to delivering all of the fluid, such as right before the fluid delivery is initiated, and a second pressure reading is obtained at a time after all of the fluid has been delivered and when the delivery mechanism is in the same position as in the previous cycle. The pressure readings are compared, and an occlusion alarm is generated if the pressure readings are the same.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for detecting occlusions in an infusion pump and particularly in an insulin pump. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1A:
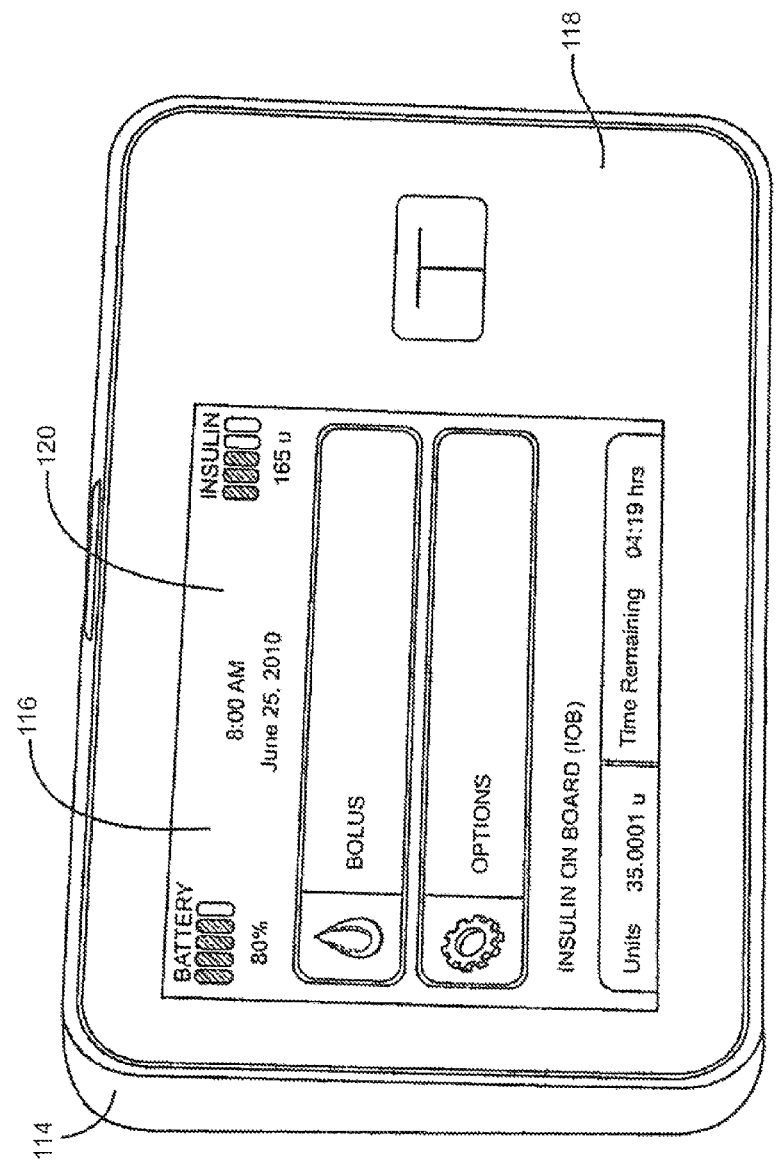
FIG. 1A is a front perspective view of an embodiment of a portable infusion pump system.
Figure 1B:
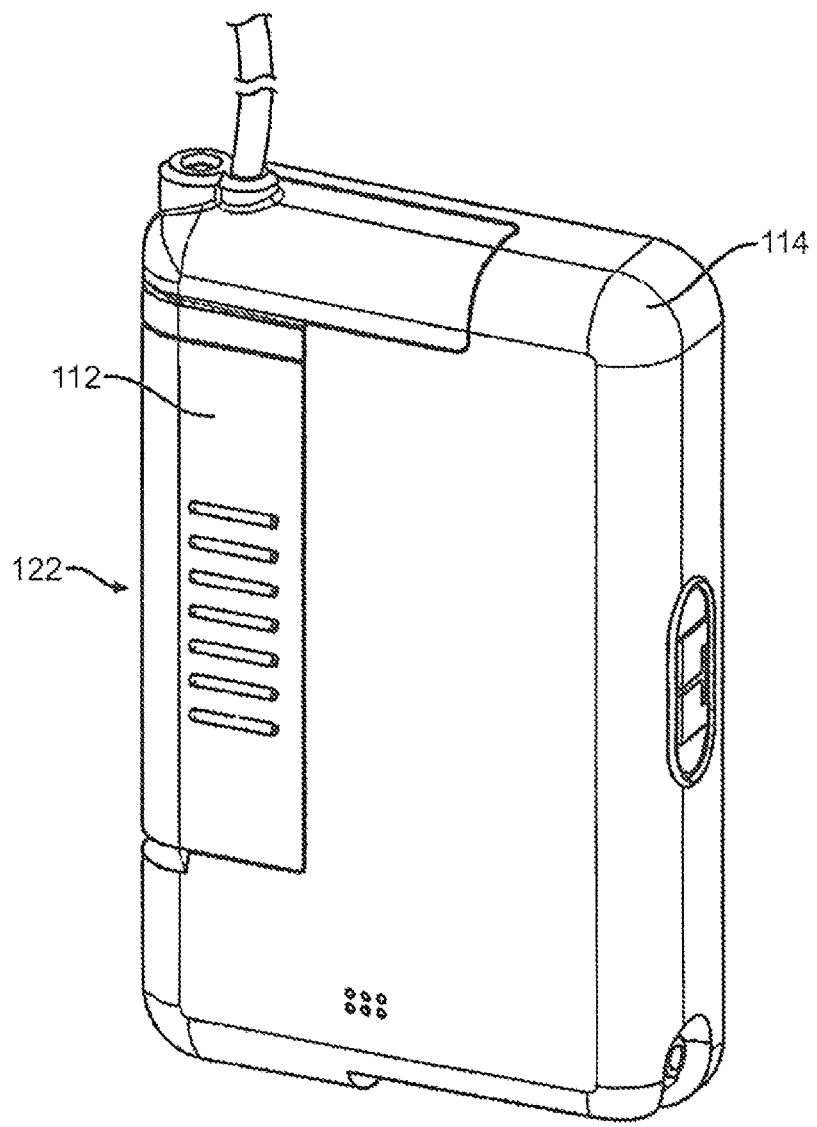
FIG. 1B is a rear perspective view of the infusion pump of FIG. 1A, including an attached infusion cartridge.

FIGS. 1A-1D depict an embodiment of a portable infusion pump system 110 including an infusion cartridge 112 and pump device 114. Infusion cartridge 112 can be a reversibly removable and interchangeable element that may be inserted into different pump devices. Referring to FIG. 1A, a front view of the pump device 114 is depicted and includes a user friendly user interface 116 on a front surface 118 of the pump device 114. The user interface 116 includes a touch sensitive screen 120 that may be configured to display a variety of screens used for displaying data, facilitating data entry by a patient, providing visual tutorials, as well as other interface features that may be useful to a patient operating the pump device 114. FIG. 1B is a rear view of the pump device 114 and illustrates the detachable installment of the infusion cartridge 112 in a slot 122 of the pump device 114 which is configured to accept the cartridge 112.

Figure 1C:
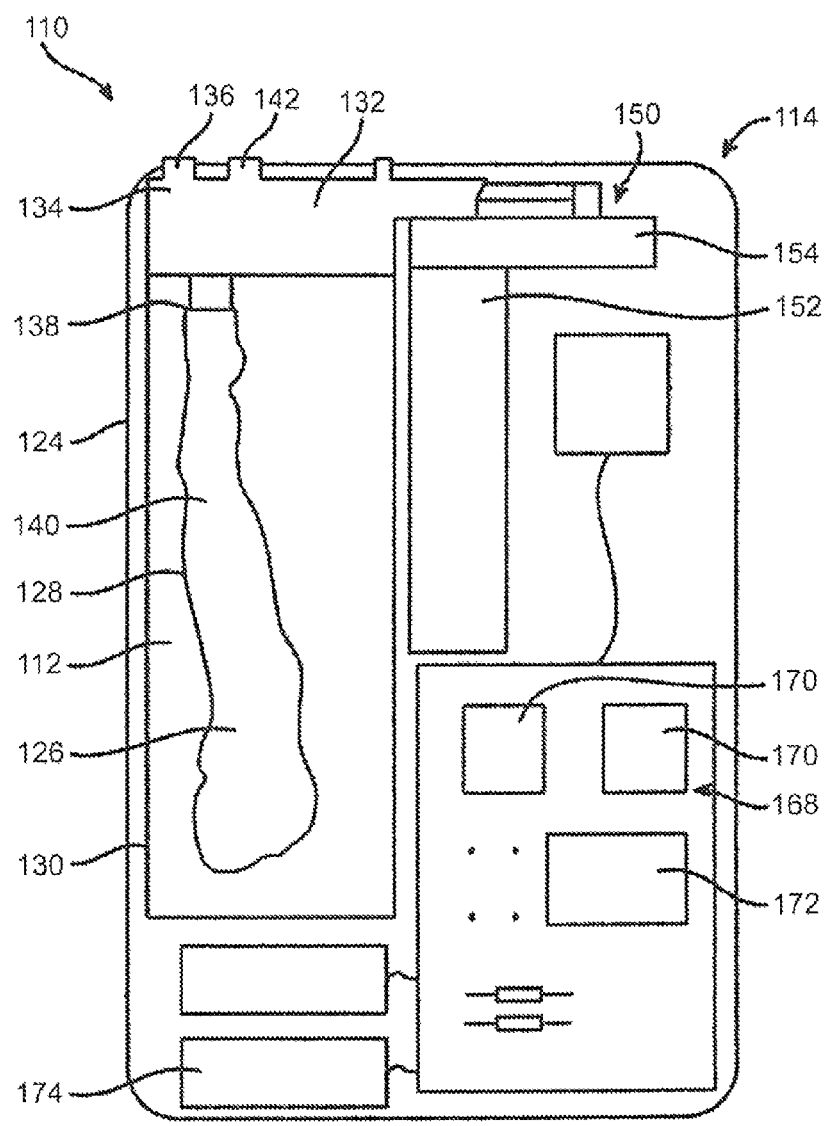
FIG. 1C is a rear schematic view of an interior of the infusion pump and cartridge embodiments of FIGS. 1A and 1B.

FIG. 1C is a schematic view of an open housing 124 of the pump device 114 depicting components that may be included in embodiments of the pump device 114. The cartridge 112 may include a fluid interface configured to receive a fluid such as collapsible reservoir 126. The collapsible reservoir 126 may be formed from a flexible material or membrane 128 that is disposed about an interior volume of the reservoir 126. The cartridge 112 also includes a substantially rigid container 130 sealed around the flexible material of the collapsible reservoir 126. A disposable delivery mechanism 132 is disposed within the disposable cartridge 112 and may have a fill port 134 with a re-sealable septum 136 sealed over the fill port 134, a reservoir inlet port 138 in fluid communication with an interior volume 140 of the collapsible reservoir 126, a fluid dispense port 142 in fluid communication with a bore 144 of the delivery mechanism 132, a vent inlet port 146 and a vent outlet port 148 both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

The cartridge 112 may be releasably and operatively secured to a housing 124 of the pump device 114. The housing 124 may be configured to house a drive mechanism 150 including a motor 152 and gear box 154 disposed in the housing 124 and detachably coupled to a spool member 156 of the delivery mechanism 132. At least one pressure sensor 158 may be disposed in a volume 160 between an outside surface 162 of the flexible material or membrane 128 of the collapsible reservoir 126 and an inside surface 164 of the substantially rigid shell or case 130. This interior volume 160 is typically scaled but can be selectively vented to the atmosphere. The graphic user interface 116 may be operatively coupled to a controller 168, which may include at least one processor 170, a memory device 172 and connective circuitry or other data conduits that couple the data generating or data managing components of the device. A power storage cell in the form of a battery 174 that may be rechargeable may also be disposed within the housing 124. Data generating or managing components of the device may include the processor(s) 170, the memory device 172, sensors 158, including any pressure or temperature sensors, the GUI 166 and the like.

Figure 1D:
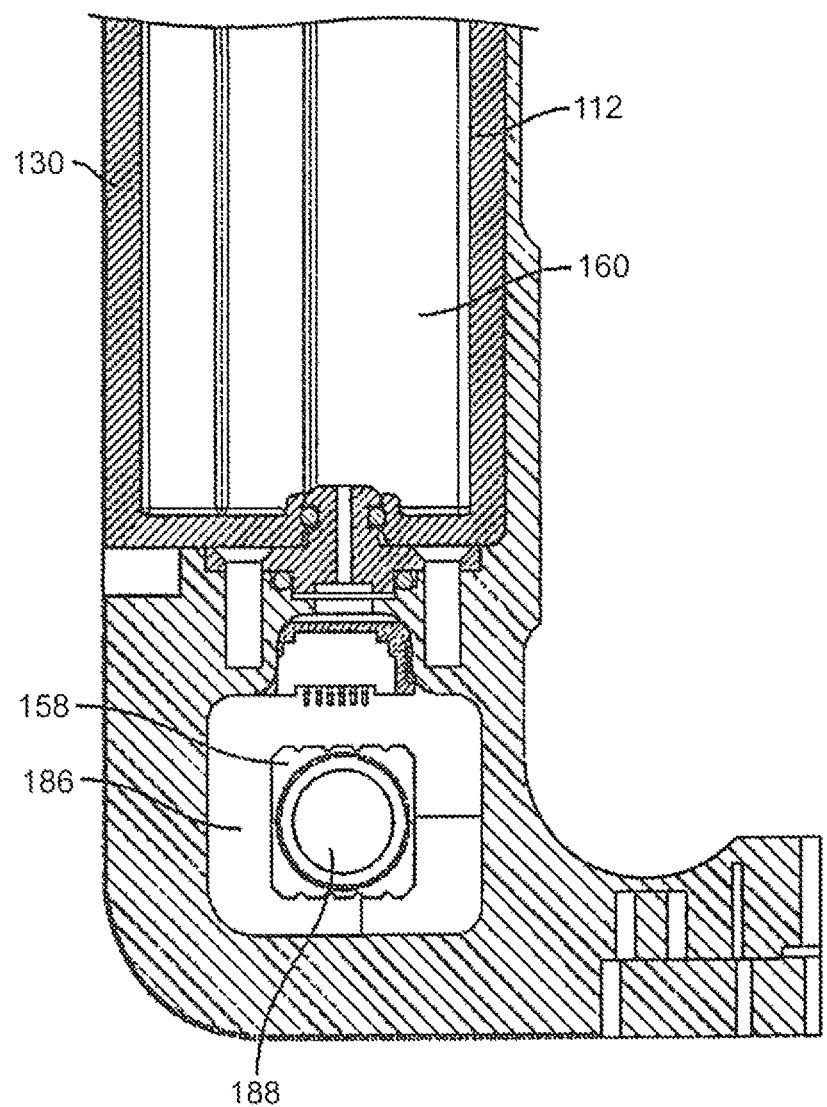
FIG. 1D is a partial sectional view of the infusion cartridge and pump device of FIGS. 1A and 1B.

The pressure inside the infusion cartridge 112, and particularly the interior volume 160 of the infusion cartridge 112, may be measured by a pressure sensor 158 disposed in the infusion cartridge 112 or in the pump device 114 in a volume, such as pocket 186 as shown in FIG. 1D. Pocket 186 is an interior volume disposed within the pump device 114 and in fluid communication with an interior volume of the fluid cartridge 112. The pocket 186 is in sealed relation with the interior volume 160 of the cartridge. As such, a pressure sensor 158 disposed within the volume of the pocket 186 will read the pressure of the volume 160 in the cartridge, but can remain with the pump device 114 after disposal of the disposable cartridge 112. This configuration lowers the cost of the cartridge while providing for pressure measurement within the cartridge 112. In some embodiments, data from the pressure sensor 158 may be used to provide a measurement of how much insulin or other medicament is being delivered by the first pump device 114. Alternatively, the pressure sensor 158 can be disposed within the cartridge directly in the sealed volume 160.

The pump device 114 can also include a thermistor or other temperature sensor 188 including an optical or infrared sensor that measures the temperature of the insulin or other medicament within the reservoir 126 upon coupling the infusion cartridge 112 with the pump device 114. Taking the temperature of the air may be important in measuring how much insulin or other medicament is in the fluid reservoir. In some embodiments, the thermistor or other temperature sensor 188 is positioned in the pocket 186 such that it can measure the temperature of the air in the pocket 186 as shown in FIG. 1D. As noted above, the pocket 186 may also include a pressure sensor 158 coupled to the controller 168 for measuring pressure within the pocket 186 and volume 160. Because the air in the pocket 186 is in fluid communication with the residual air within the chamber 160, the temperature and pressure of the air in the infusion cartridge 112 surrounding the fluid reservoir 126 may be equal or approximately equal to the temperature and pressure of the air in contact with the temperature sensor 188 and pressure sensor 158. In turn, the temperature sensor 188 may provide a relatively accurate measurement of the temperature of the insulin or other medicament within the reservoir 126.

Referring to FIGS. 2-7, an embodiment of the delivery mechanism 132 is depicted in a fluid delivery cycle sequence wherein fluid from the interior volume of the reservoir 126 is drawn into the bore 220 of the delivery mechanism 132 and dispensed from the dispense outlet port 142.

Referring again to FIG. 2, a portion of the fluid reservoir cartridge 112 including a delivery mechanism 132 is shown in section as well as a portion of a drive mechanism 150 of an infusion pump. The disposable fluid cartridge 112 includes the delivery mechanism 132 which has a delivery mechanism body 236 and a bore 220 disposed in the delivery mechanism body 236. The bore 220, which may have a substantially round transverse cross section, includes a distal end 238, a proximal end 240 disposed towards the drive mechanism 150 of the infusion pump 114, an interior volume 242, a reservoir inlet port 138, a fluid dispense port 142, a vent inlet port 146 and a vent outlet port 148. The spool 156, which may also have a substantially round transverse cross section, is slidingly disposed within the bore 220 and forms a collapsible first volume 244 and a vent second volume 246 between the bore 220 and an outside surface 266 of the spool 156.

The collapsible first volume 244 of the delivery mechanism 132 may be positionable to overlap the reservoir inlet port 138 independent of an overlap of the fluid dispense port 142. The collapsible first volume 244 may be formed between a first seal 248 around the spool 156, a second seal 250 around the spool, an outer surface of the spool body between the first and second seal 250 and an interior surface 252 of the bore 220 between the first and second seal 248 and 250. The first and second seals 248 and 250 are axially moveable relative to each other so as to increase a volume of the collapsible volume 244 when the first and second seals 248 and 250 are moved away from each other and decrease the collapsible volume 244 when the seals 248 and 250 are moved closer together.

The second seal 250 is disposed on a main section 254 of the spool 156 of the delivery mechanism 132 and moves in conjunction with movement of the rest of the spool. A proximal end 196 of the spool 156 is coupled to a ball portion 194 of a drive shaft 190 of the drive mechanism 150 of the pump device 114. The drive mechanism 150 includes a rack and pinion 192 mechanism actuated by an electric motor 152 through a gear box 154. As such, the second seal 250 moves or translates axially in step with axial translation of the spool 156 and drive shaft 190. The first seal 248, however, is disposed on a distal section 258 of the spool 156 which is axially displaceable with respect to the main section 254 of the spool 156. The distal section of the spool 156 is coupled to the main section of the spool by an axial extension 260 that is mechanically captured by a cavity 261 in the main section 254 of the spool 156. This configuration allows a predetermined amount of relative free axial movement between the distal section 258 of the spool and the nominal main section 254 of the spool 156.

For some embodiments, a volume of a "bucket" of fluid dispensed by a complete and full dispense cycle of the spool 156 may be approximately equal to the cross section area of the bore 220 multiplied by the length of displacement of the captured axial extension of the spool 156 for the distal section 258. The complete bucket of fluid may also be dispensed in smaller sub-volumes in increments as small as a resolution of the drive mechanism 150 allows. For some embodiments, a dispense volume or bucket defined by the complete collapsible volume 244 of the delivery mechanism 132 may be divided into about 10 to about 100 sub-volumes to be delivered or dispensed. In some cases, the maximum axial displacement between the distal section and main section of the spool may be about 0.01 inch to about 0.04 inch, more specifically, about 0.018 inch, to about 0.022 inch.

Figure 2:
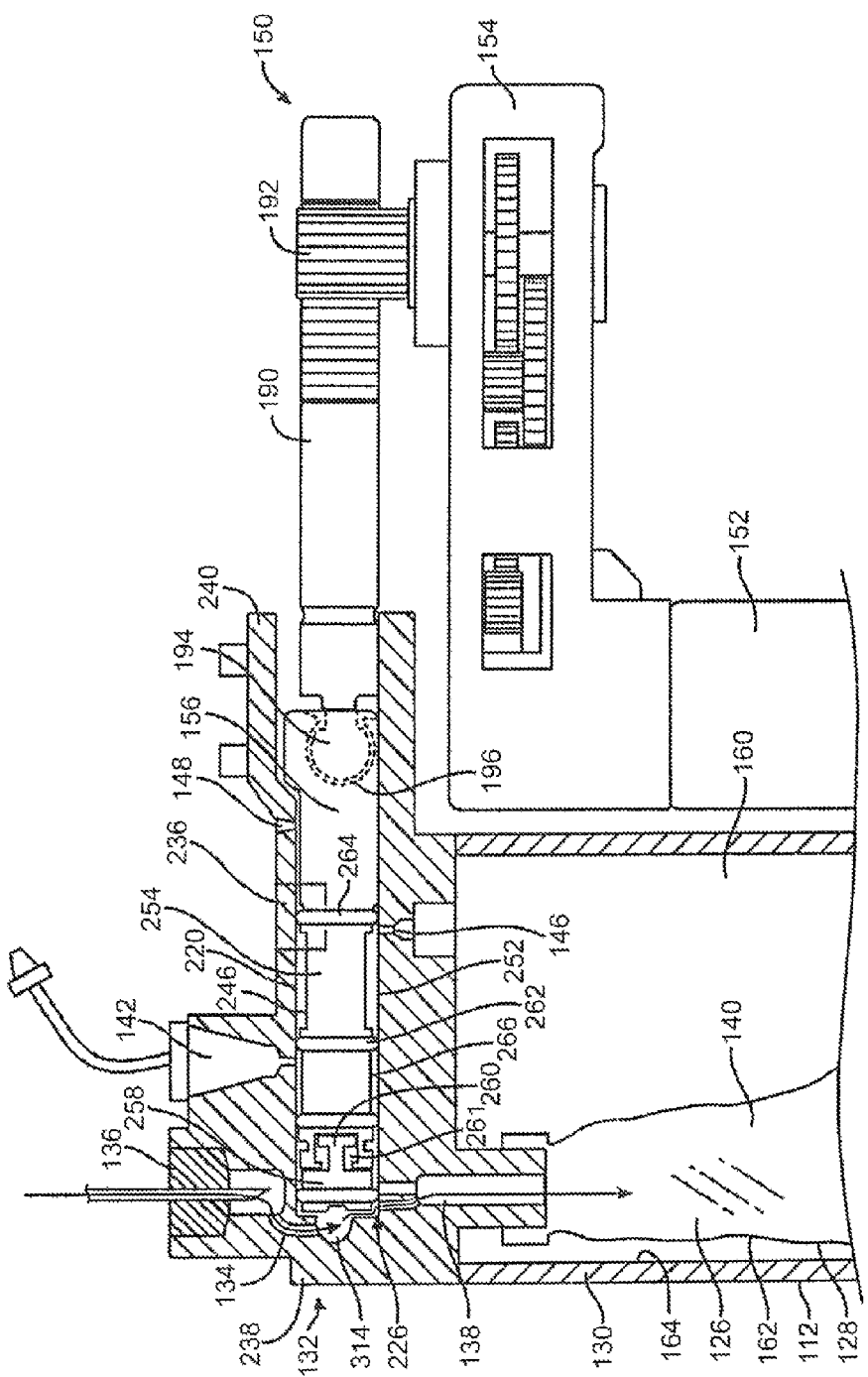
FIG. 2 is a partial sectional view of a delivery mechanism of an infusion pump with the spool of the delivery mechanism positioned at a distal hard stop for filling of the expandable reservoir according to an embodiment of the present invention.
Figure 3:
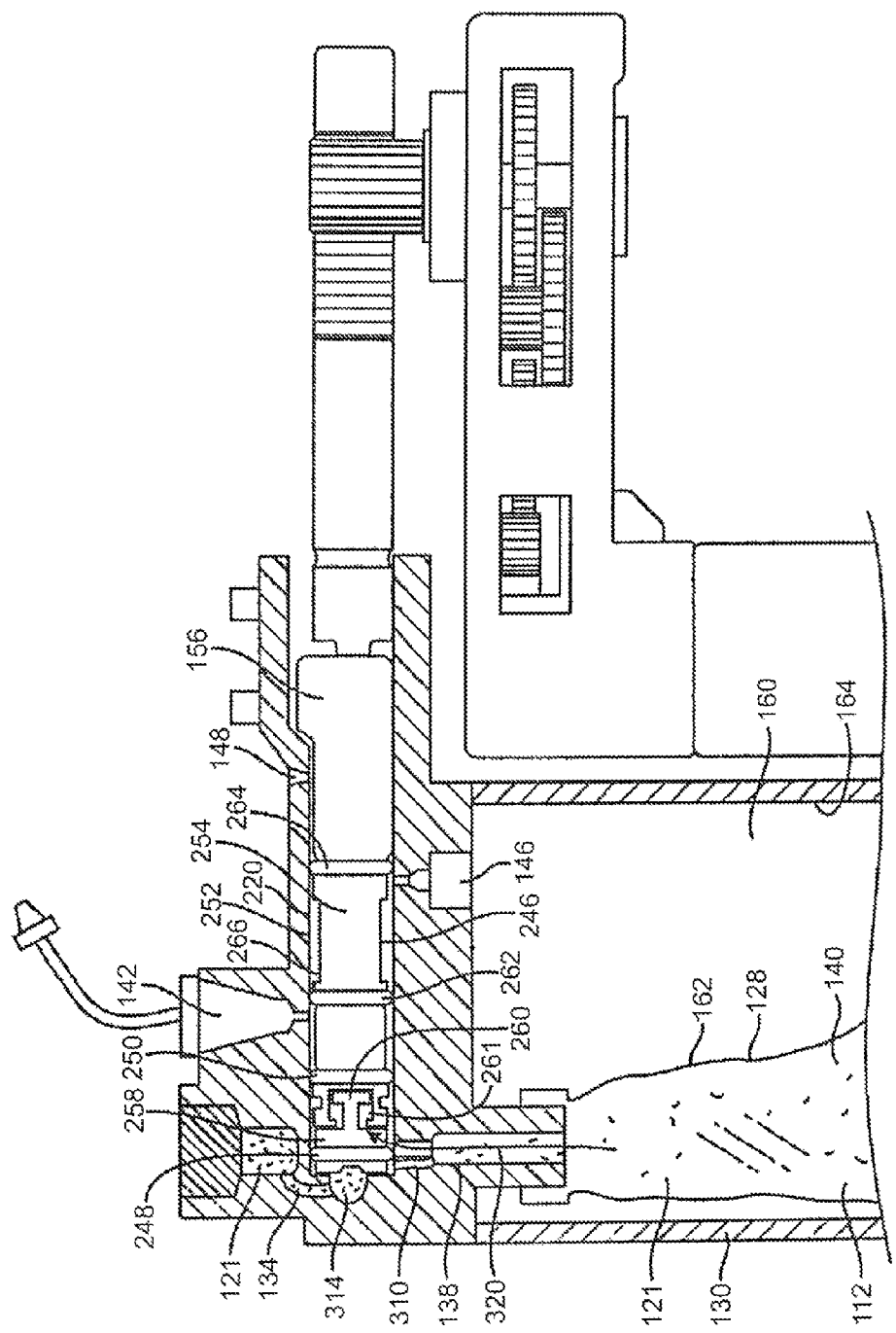
FIG. 3 is similar to FIG. 2, but with the spool of the delivery mechanism positioned for filling of a collapsible volume of the spool.

In use, once the reservoir cartridge 112 of the infusion pump system 110 has been installed or otherwise snapped into place in the slot 122 of the pump device 114, the interior volume 140 of the collapsible reservoir 126 may then be filled with a desired fluid 121 for dispensing. In order to fill the reservoir 126, the spool 156 may be translated by the drive mechanism 150 to a hard stop position 226 as shown in FIG. 2. In the hard stop position 226 the first seal 248 is disposed proximally of a relief port 310, the relief port 310 being disposed in fluid communication between a distal end 238 of the bore 220 and the reservoir volume 140. In the hard stop position, the first seal 248 is also disposed distally of the reservoir inlet port 138. In the hard stop position, a distal end 316 of the spool 156 is contacting the distal end 238 of the bore 220 or a shoulder portion 312 of the distal end 238 of the bore 220 to prevent any further distal displacement of the spool 156.

A reservoir fill port 134 is disposed on a top portion of the bore 220 substantially opposite the bore 220 of the reservoir inlet port 138. With the spool 156 and seals 248, 250, 262 and 264 thereof so positioned, a patient may then obtain an amount of a desired fluid to be dispensed. In some cases, if the desired fluid to be dispensed is insulin or other suitable medicament, the patient 127 typically stores the insulin in a refrigerated glass container. The insulin is then accessed with a hypodermic needle 222 of a syringe device and drawn into an interior volume of the syringe (not shown). The tip of the hypodermic needle 222 of the syringe may then be pushed through a septum membrane 136 that seals the reservoir fill port 134 as shown and fluid manually dispensed from the interior volume of the syringe, through the hypodermic needle 222, through a bubble trap volume 314 in the bore 220 of the delivery mechanism 132 and into the interior volume 140 of the collapsible reservoir 126 of the cartridge 112 as shown by the arrow 318 in FIG. 2.

As discussed above with regard to other embodiments of the delivery mechanism 132, the volume 160 of the cartridge 112 disposed between an outside surface 162 of the flexible membrane 128 of the collapsible reservoir 126 and an inside surface 164 of the rigid shell 130 may include or be in operative communication with a pressure sensor 158. The pressure sensor 158 may be used to monitor the pressure within the volume 160 during the filling of the collapsible reservoir 126. The controller 168 of the pump system 114 may be programmed with information regarding the fixed volume of the rigid shell 130 of the cartridge 112 and configured calculate the volume of fluid loaded into the collapsible reservoir 126 based on the pressure rise within the rigid shell 130 upon filling of the collapsible reservoir 126. The data regarding the volume of fluid loaded into the collapsible reservoir 126 may be stored and used to calculate and display data later in the use cycle such as fluid remaining in the collapsible reservoir 126 and the like.

Once the collapsible reservoir 126 contains a desired amount of a fluid 121 to be dispensed, a dispense cycle may be initiated by driving the spool 156 with the drive mechanism 150 based on commands from a controller 168 of the pump device to a position with the collapsible first volume 244 in communication with the reservoir inlet port 138. The hard stop position depicted in FIG. 2 is such a position. If the spool 156 has been driven to this hard stop position 226 in a distal direction from previous proximal position, the friction generated between the first seal 248 of the spool 156 and the inside surface 252 of the bore 220 will have collapsed the collapsible volume 244 of the delivery mechanism 132 with the first seal 248 and second seal 250 in a least axially separated state. In this state, the collapsible volume 244 has a minimum volume. Such a state of the delivery mechanism 132 is shown in FIG. 2. Once in this pre-fill position, the spool 156 may then be driven so as to axially separate the first and second seals 248 and 250 (and the main section 254 of the spool 156 and distal section 258 of the spool 156) of the collapsible first volume 244 and draw fluid into the first volume 244 through the reservoir inlet port 138 from the reservoir 126 as shown by the arrow 320 in FIG. 3. As the fluid 121 is drawn into the collapsible volume 244, the pressure within the volume 160 decreases. As previously discussed, this drop in pressure may be used in accordance with the ideal gas law to determine the amount of material taken from the collapsible reservoir 126. An unexpected reading based on the magnitude of the translation of the main section 254 of the spool 156 may also be used to detect a failure of a portion of the delivery mechanism 132 in some cases.

Figure 4:
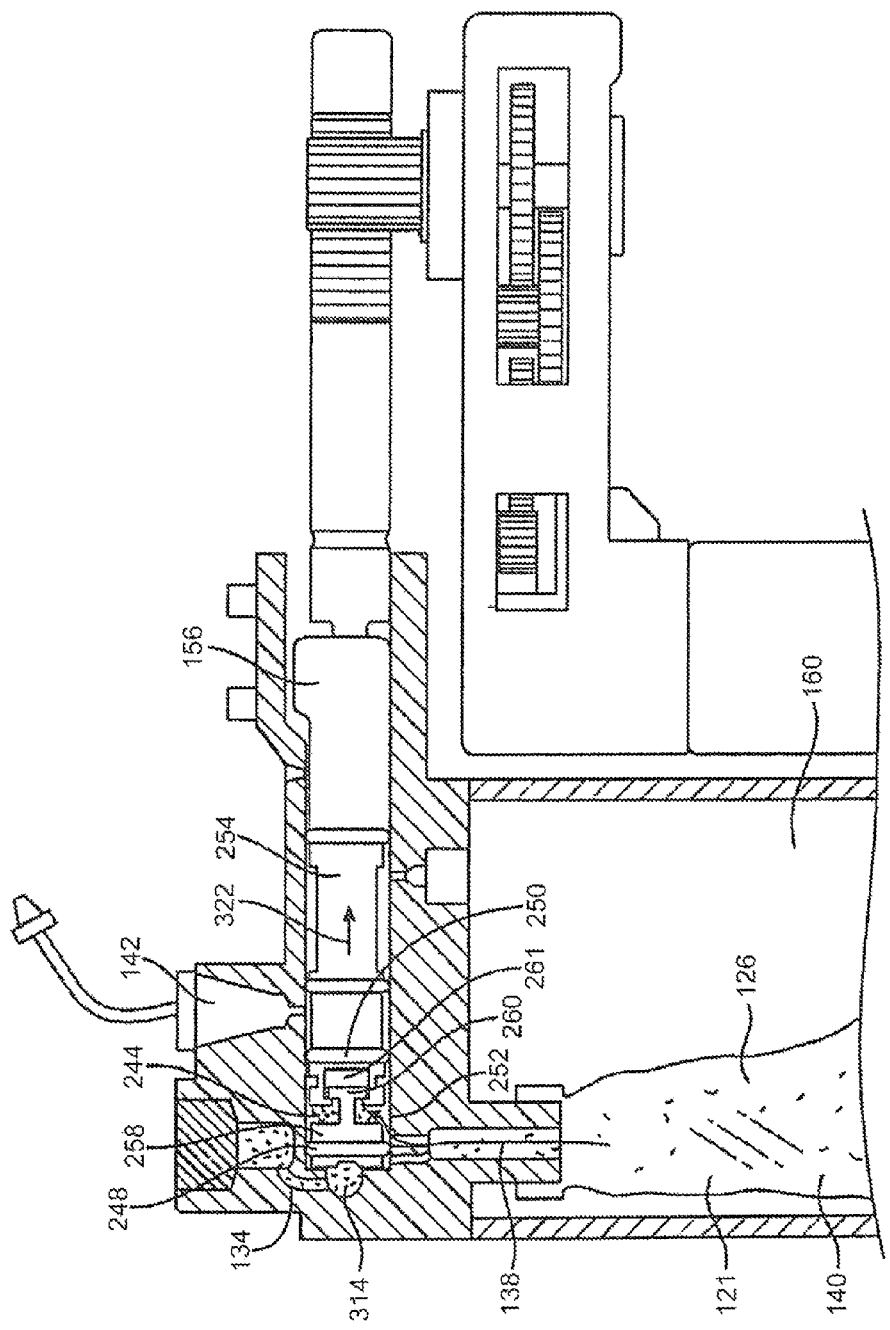
FIG. 4 is similar to FIG. 2, but with the spool of the delivery mechanism positioned after filling of the collapsible volume of the spool.
Figure 5:
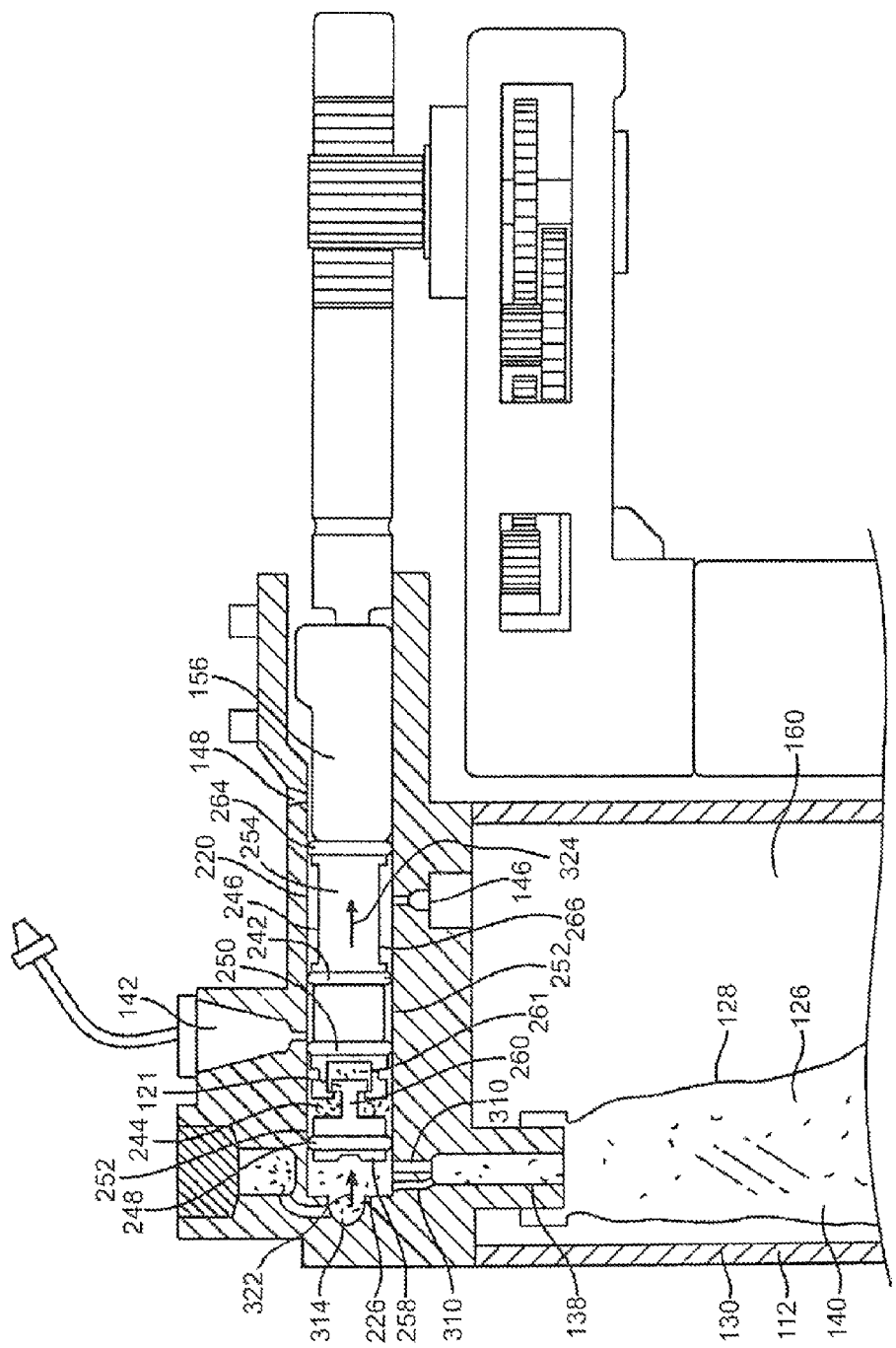
FIG. 5 is similar to FIG. 2, but with the collapsible volume of the device full of fluid being displaced proximally towards the dispense port of the device.

The collapsible volume 244 of the delivery mechanism 132 may be completely filled by proximally retracting the main section 254 and second seal 250 of the spool 156 relative to the first seal 248 and distal section 258 of the spool 156 as shown by arrow 322 on spool 156 in FIG. 4. Once filled, the spool 156 may then be driven in a proximal direction as shown in FIG. 5 wherein there are two seals 248 and 250 disposed in the bore 220 between the reservoir inlet port 138 and relief port 310 and the dispense port 142. As shown by arrow 323 and arrow 324 in FIG. 5, both the main section 254 and distal section 258 of the spool 156 are proximally retracted together. The captured axial extension of the distal section 258 by the main section 254 pulls the distal section along without axial displacement between the main section 254 and distal section 258 of the spool 156. The dispense port may be in fluid communication with a subcutaneous portion of a patient's body. The delivery mechanism 132 always includes at least one seal 248 or 250 disposed in the bore 220 between the reservoir volume 140 and material 121 disposed therein and the dispense port 142 in order to prevent a free flow condition wherein the material 121 in the reservoir 126 is in uninterrupted communication with the patient's body.

Figure 6:
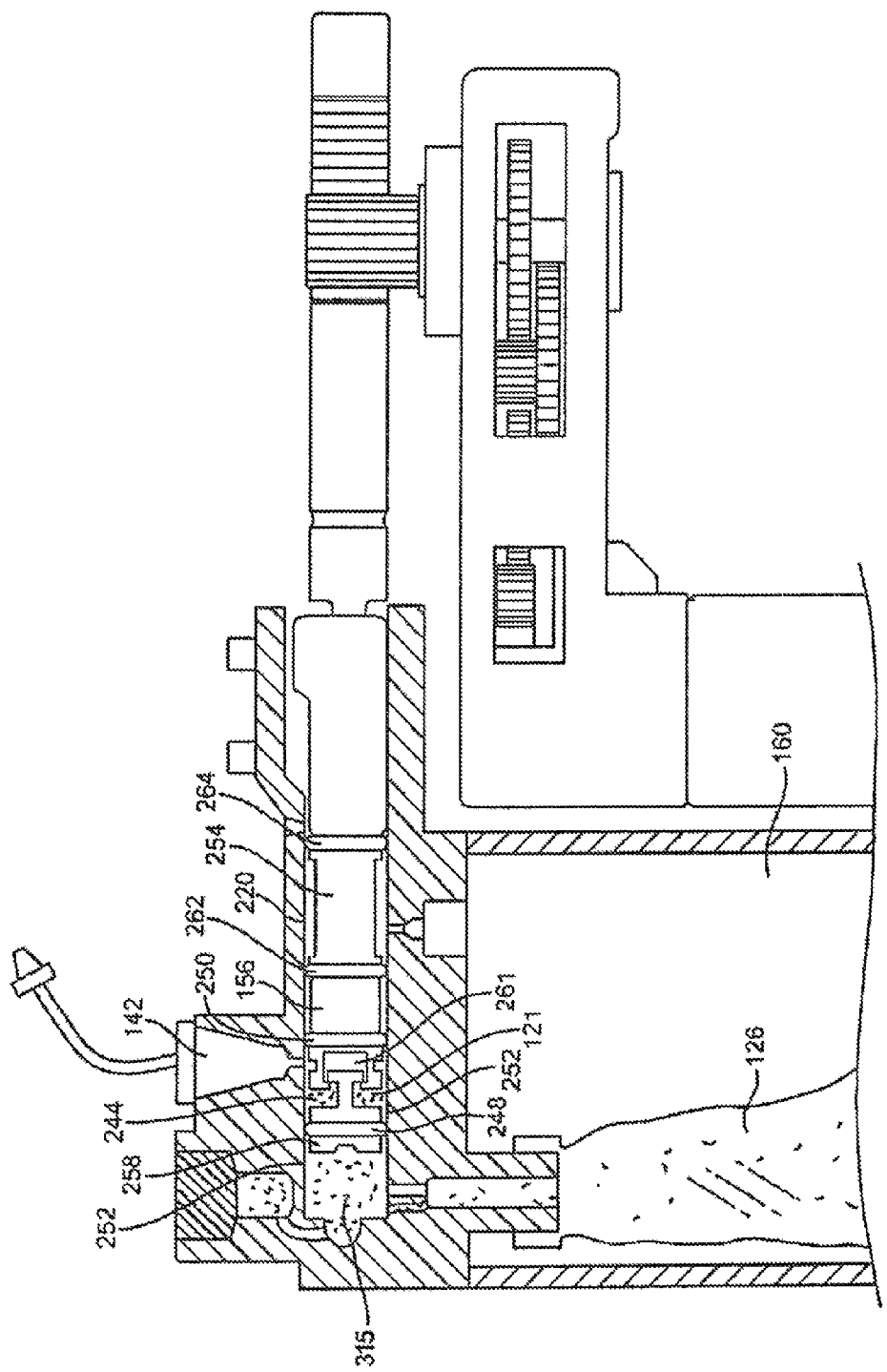
FIG. 6 is similar to FIG. 2, but with the spool of the delivery mechanism positioned prior to delivery of fluid into the dispense port from the collapsible volume of the spool.
Figure 7:
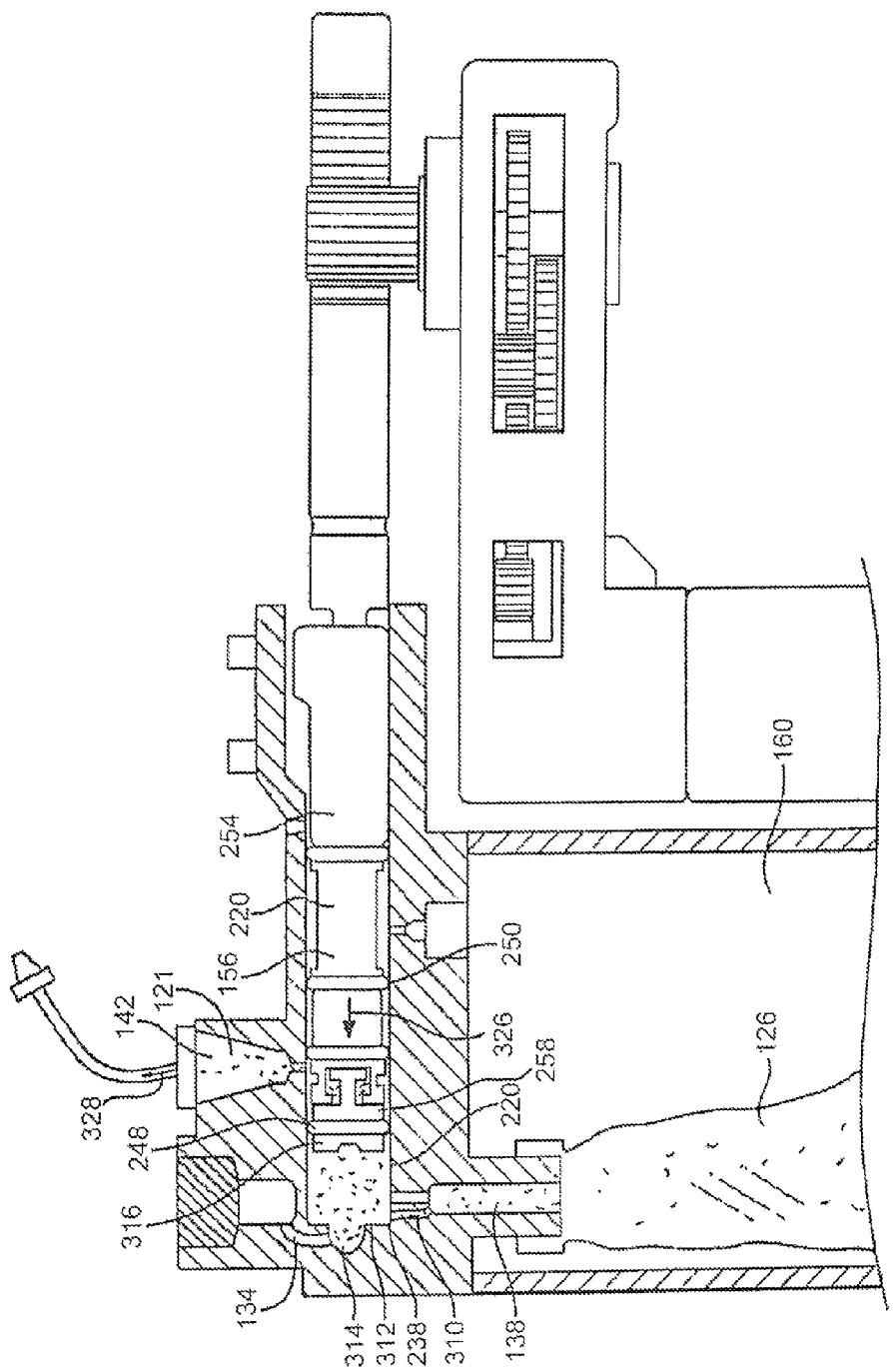
FIG. 7 is similar to FIG. 2, but with the spool of the delivery mechanism positioned after delivery of fluid from the collapsible volume of the spool into the dispense port.

Once filled, the spool 156 and filled collapsible volume 244 may be proximally displaced with the drive mechanism 150 to a position with the collapsible first volume 244 in communication with the fluid dispense port 142 of the bore 220 as shown in FIG. 6. Once the spool 156 is positioned as depicted in FIG. 6, the main section of the spool 156 may then be axially driven in a distal direction by the drive mechanism 150 with the distal section 258 of the spool remaining stationary or substantially stationary. This axial distal movement of the main section 254 as indicated by arrow 326 on the spool 156 depicted in FIG. 7, serves to at least partially collapse the collapsible first volume 244. Collapsing the first volume 244 of the delivery mechanism 132 dispenses fluid from the collapsible first volume 244 through the fluid dispense port 142 as shown by the arrow 328 in FIG. 7. Once all fluid from the collapsible first volume 244 is dispensed in this manner, additional cycles as described above can be completed to provide additional insulin to the patient. Further details on the operation and configuration of such an infusion pump can be found in U.S. Patent Application Publication No. 2011/0144586, which is hereby incorporated by reference herein.

Figure 8:
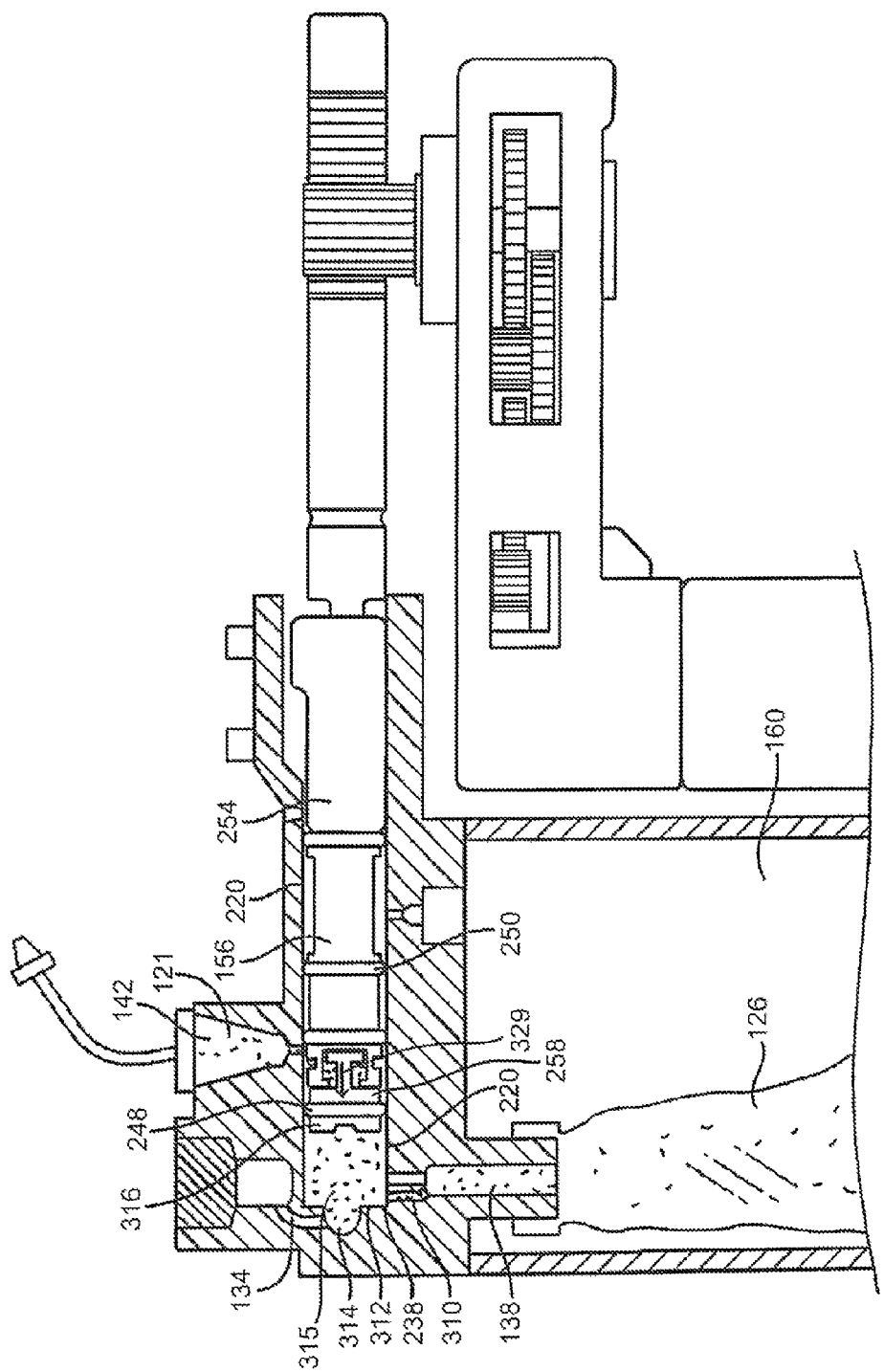
FIG. 8 is similar to FIG. 2, but depicting a condition of an occlusion present in the delivery line.

The above description relates to the use of a portable or ambulatory pump device 114 and cartridge 112 when properly operating to draw fluid from the reservoir 126 and dispense it to a patient. As described above with reference to FIG. 7, when the main section 254 of the spool 156 is moved distally to collapse the first volume 244 to dispense the fluid, the distal section 256 of the spool 156 is stationary. However, there are certain conditions that will prevent the device 114 from operating properly. For example, an occlusion in the line delivering the fluid from the device to the patient will prevent the fluid from traveling along path 328 to the patient depicted in FIG. 7. Thus, as the main section 254 of the spool 156 is advanced distally, rather than propelling the fluid out the fluid dispense port 142, pressure builds up in the patient line and ultimately the pressure is exerted on the distal section 258 of the spool. When this pressure exceeds the frictional force of the seal 248, the distal section 258 of the spool 156 is also moved distally as shown by arrow 329 in FIG. 8.

This movement of the distal section 258 of the spool 156 can used to determine whether or not an occlusion is present in the patient line because the movement will cause the pressure in the reservoir to react differently indicating that an occlusion is present. Pressure readings taken during certain predetermined times of either basal insulin delivery or bolus delivery can be used by the processor 170 to identify an occlusion based on movement of the distal section 258.

During basal insulin delivery, typically the "bucket" of insulin is filled as shown in FIGS. 2-5 and then the insulin in the bucket is slowly delivered to the patient a portion at a time. For example, the motor may be activated to move the main portion 254 of the spool 156 to deliver a portion of the insulin every five minutes over the course of one or several hours. Thus, the bucket may only be filled once every few hours. As described above, if there is an occlusion in the line, the force of the motor 152 advancing the spool 156 will, instead of dispensing fluid, cause the distal section 258 of the spool 156 to move distally in the bore 220 as shown by the arrow 329 in FIG. 8. This movement will force some of the fluid in the space 315 back into the reservoir 126. This change in volume of the reservoir 126 will correspondingly alter the pressure in the interior volume 160 of the cartridge 112.

Thus, pressure measurements of the interior volume 160 made by the pressure sensor 158 can be utilized by the processor 170 to determine if there is an occlusion in the patient line as reflected by a change in pressure. In one embodiment, the pressure is monitored immediately before and immediately after the motor 152 is activated to move the spool 156 to dispense a portion of insulin for the basal insulin delivery. If the pressure readings are the same, then the insulin was delivered through the patient line and there is no occlusion. If there is an occlusion that prevented insulin from being delivered to the patient and caused the distal section 258 to move during the operation, then the pressure readings will change. These changed readings, or accumulation of readings, indicate that an occlusion is present due to movement of the distal section causing additional insulin to be forced back into the reservoir 126.

If the pressure readings indicate that an occlusion is present, the processor 170 can cause an alarm indicating the presence of an occlusion to be generated and displayed to the user on the GUI 166. The pump may also automatically cease operation upon generation of such an alarm until the user indicates that the occlusion has been corrected. Because the pressure readings taken before and after the motor move to deliver a portion of the bucket are taken with only a short period of time elapsing—as opposed to being taken each time the bucket is filled or completely emptied—any effects from long term systematic sensor changes are minimized. In one embodiment, an occlusion alarm can be generated when the before and after pressure readings are different for a single motor move. In other embodiments, the processor 170 may require that the pressure readings be different for two or more consecutive motor moves before indicating an occlusion in order to reduce signal noise. In addition, if a sensor has been inactive for a period of time, it may take some time for the measurements of the sensor to reach a desired degree of accuracy, so it may be desirable to begin comparing pressure values only after the sensor has been operating for a certain period of time. Same or constant pressure in this context may mean exactly the same pressure. Same or constant pressure can also mean pressures within a defined threshold of each other.

Figure 9:
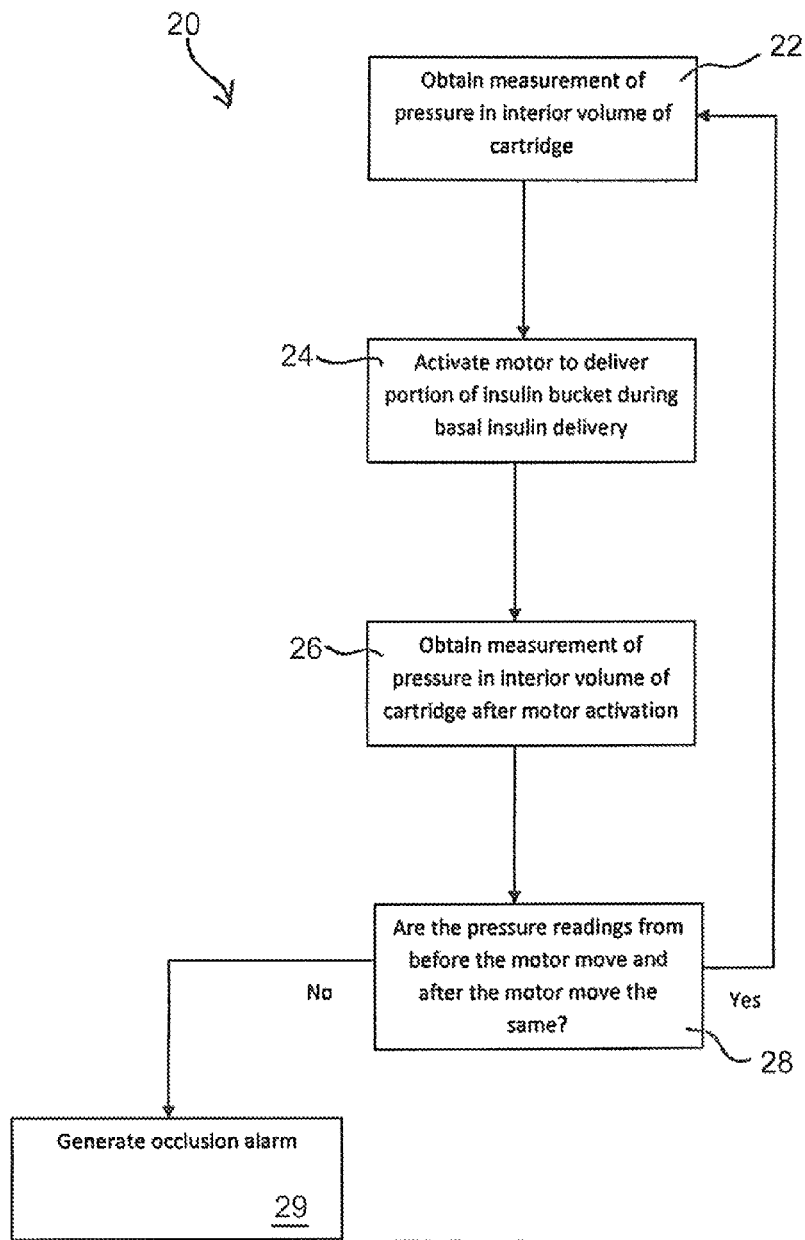
FIG. 9 is a flowchart of a method for detecting occlusions in a portable infusion device during basal insulin delivery according to an embodiment of the present invention.

FIG. 9 depicts a flowchart of a method of detecting occlusions in a portable infusion pump during basal insulin delivery 20 according to an embodiment of the present invention. At step 22, a measurement of pressure in the interior volume of an insulin cartridge is made prior to activating a motor to deliver a portion of a bucket of insulin to a patient. The motor is then activated at step 24 to deliver the portion of insulin to the patient. At step 26, a measurement of the pressure in the interior volume of the cartridge is obtained after the motor move. Preferably, this measurement is taken immediately following the motor being powered down. The pressure readings before and after the motor move are compared by the processor at step 28. If the pressure readings are the same, this is indicative of there being no occlusion in the patient delivery line and the method reverts back to step 22 for a subsequent motor move. If the pressure readings are not the same, the comparison indicates that there is an occlusion in the patient line. An occlusion alarm can then be generated at step 29. The occlusion alarm can be an audio alarm, visual alarm, tactile alarm, or some combination of these. In some embodiments, the process will not proceed to step 29 to generate the alarm unless the pressure readings are different for more than one consecutive motor move. As noted above, the pressure readings being the "same" can mean that the pressure readings are exactly the same when rounded to a desired degree of precision or that the values are within a predefined threshold amount or percentage of each other.

In some embodiments, the pressure readings accumulated during motor moves are compared to a baseline value. For example, the difference between each pressure reading and the baseline is calculated. The differences can be summed and/or averaged, and if the difference is greater than a threshold amount from the baseline, an occlusion is detected. The baseline and/or threshold values can be varied based on the relative volume of air in the cartridge. When there is a greater amount of air in the cartridge, the pressure reading is smaller. Thus, a lower threshold deviation from the baseline can trigger an occlusion detection. In this manner, the threshold and baseline values can be determined based on the ideal gas law. In other embodiments, rather than comparing pressure readings to a baseline, the pressure readings are compared directly to each other and a threshold difference between readings, or an accumulation of readings, that indicates an occlusion can be calculated as described above.

In bolus delivery, the volume of fluid in the reservoir decreases by a fixed amount with each subsequent cycle of the delivery mechanism to draw fluid from the reservoir 126 into the bore 220 and then deliver it to the patient. Correspondingly, the pressure in the interior volume 160 of the cartridge 112, as measured by the pressure sensor 158, drops by a fixed amount with each subsequent cycle as shown by line 12 in FIG. 10. In contrast, when an occlusion is present in the patient line, fluid is not being dispensed out of the device and therefore each subsequent operation of the motor does not draw additional fluid from the reservoir. Therefore, the pressure in the interior volume 160 of the cartridge after each subsequent operation remains constant as shown by the line 14 in FIG. 10. Line 14 reflects that the pressure will drop when the frictional force holding the distal section 258 of the spool 156 in place is overcome moving the distal section 258 distally, but will build back up again each time the main section 254 of the spool 156 is advanced for the operation intended to dispense fluid out of the dispense port 142.

Figure 10:
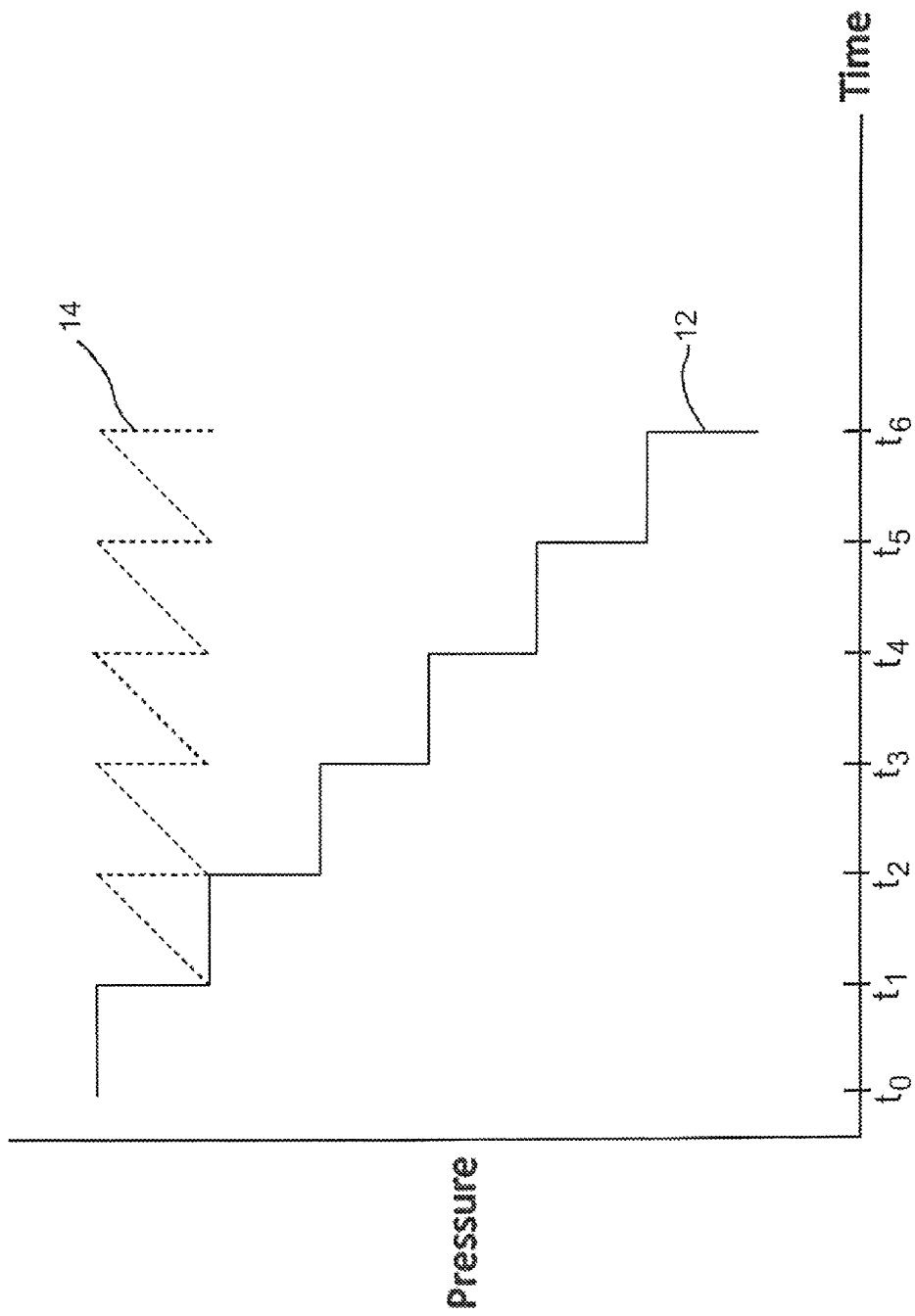
FIG. 10 is a graph of cartridge pressure versus time for an infusion device such as the infusion device of FIG. 2 according to an embodiment of the invention.

In FIG. 10, the time markings $t_0$ through $t_6$ indicate times at which pressure readings are taken that are each taken at an identical stage in the bolus delivery process. In one embodiment, the pressure readings are taken after the bolus has been delivered and the device is in the "ready to fill" position such as in FIG. 2 and/or FIG. 3. In other embodiments, pressure readings can be taken at different times during the operational sequence of the pump. Preferably, however, the readings are all taken at the same time during each subsequent cycle to allow for more accurate comparison of readings.

Thus, by monitoring pressure in the interior volume 160 of the cartridge 112 during subsequent bolus cycles, it can be determined by the processor 170 whether an occlusion is present in the line delivering fluid to the patient. If each subsequent pressure reading is dropping by a constant amount, there is no occlusion and the system is operating normally. If the pressure readings remain constant at each of two or more subsequent time intervals, then an occlusion is present. Long term systematic effects on the sensors are minimized because all of the insulin in the bucket is delivered immediately, so there is not a significant time gap between readings. This is particularly true when the measurements are taken at the "ready to fill" position of the delivery mechanism, because the mechanism will again be in the ready to fill position upon completing the bolus.

If the pressure readings indicate that an occlusion is present, an alarm indicating the presence of an occlusion can be generated and displayed to the user on the GUI 166 by the processor 170. The pump may also automatically cease operation upon generation of such an alarm until the user indicates that the occlusion has been corrected. In one embodiment, an occlusion alarm can be generated when two consecutive pressure readings are constant. In other embodiments, the pump may require more than two pressure readings before indicating an occlusion in order to reduce signal noise. Constant pressure in this context may mean exactly the same pressure. Constant pressure can also mean pressures within a defined threshold of each other.

Figure 11:
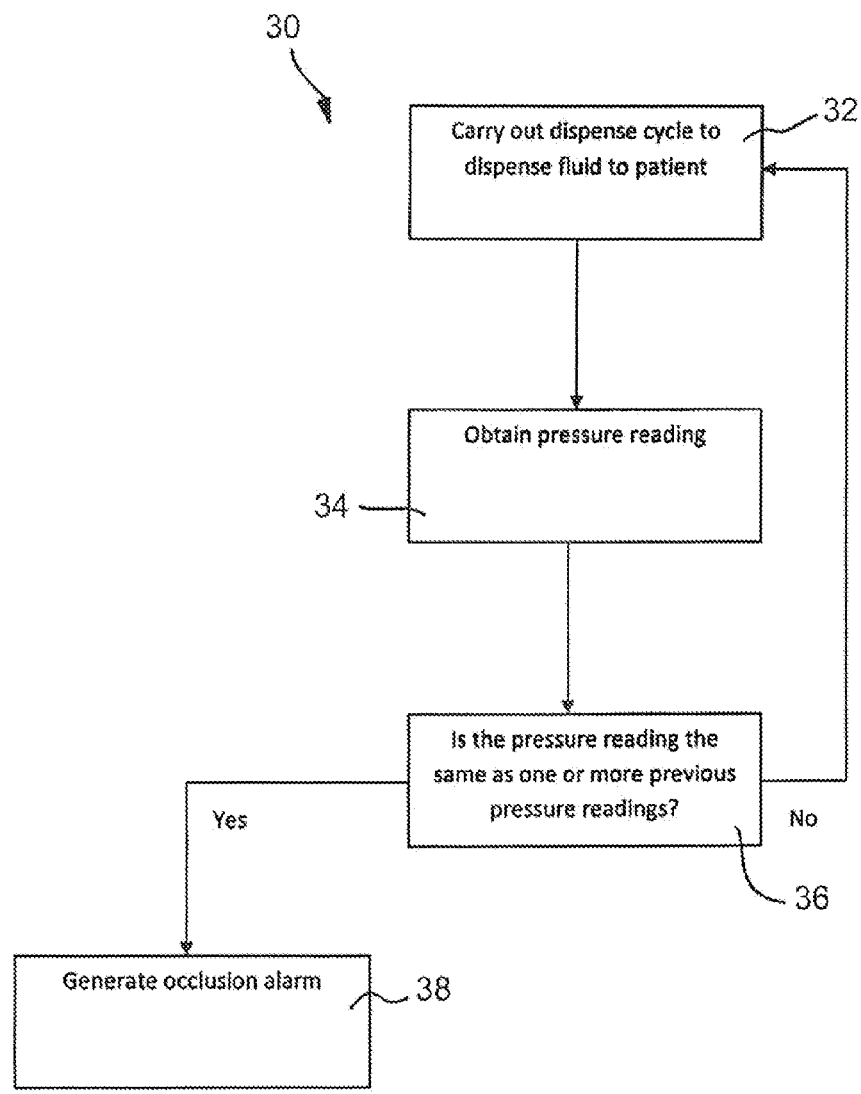
FIG. 11 is a flowchart of a method for detecting occlusions in a portable infusion device during bolus insulin delivery according to an embodiment of the present invention.

FIG. 11 depicts a flowchart of a method of detecting an occlusion in an infusion pump system 30 according to an embodiment of the present invention. At step 32, a dispense cycle for delivering a bolus of fluid to a patient, such as described herein, is carried out. A pressure reading is obtained at some point before, during or after the dispense cycle at step 34. In one embodiment, the pressure reading is immediately following dispensing the fluid to the patient so that the delivery mechanism is once again in the "ready to fill" position. The pressure can be the pressure in a housing of a cartridge of the portable infusion system containing the fluid reservoir, At step 36, the pressure reading is compared to one or more previous pressure readings by the processor 170. Typically, each compared pressure reading will be taken at the same stage of the dispense cycle as previous readings. For example, the previous pressure reading may have been taken immediately prior to filling the bucket of insulin. If the pressure readings are not the same, an occlusion alarm can be generated at step 38. Occlusion alarm can be an audio alarm, visual alarm, tactile alarm, or some combination of these. In some embodiments, the process will not proceed to step 38 to generate the alarm unless the current pressure reading is the same as more than one previous pressure reading. As noted above, the pressure readings being the "same" can mean that the pressure readings are exactly the same when rounded to a desired degree of precision or that the values are within a predefined threshold amount or percentage of each other.

In some embodiments, an occlusion detection system and method as described herein can account for physical conditions of the pump that falsely indicated an occlusion. Thus, if a single reading or limited number of readings indicates that an occlusion is present, the system can determine whether or not the reading is a false reading based on a condition of the device. Examples of such conditions include the cartridge reservoir being empty, the cartridge being dislodged or otherwise removed between readings or rapid changes in ambient temperature or pressure.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion system, comprising:
a disposable infusion cartridge, the infusion cartridge including a collapsible reservoir for containing a fluid and a substantially rigid shell disposed over the collapsible reservoir and forming, an interior volume between an outside surface of the collapsible reservoir and an inside surface of the shell, the disposable infusion cartridge further including a delivery mechanism having a spool slidingly disposed in a bore, the spool including as main section and a distal section axially displaceable relative to the main section with a collapsible volume formed between a seal on the main section and a seal on the distal section;
a pump device configured to selectively receive the infusion cartridge and cooperate with the infusion cartridge to deliver fluid from the reservoir to the patient, the pump device including a drive mechanism powered by a motor and selectively engageable with the spool to impart controlled axial movements to the spool to deliver fluid from the cartridge to the patient
a pressure sensor located in one of the infusion cartridge and the pump, the pressure sensor in communication with the interior volume of the infusion cartridge; and
a processor located in one of the infusion cartridge and the pump wherein the processor is adapted to:
obtain a first pressure reading of the pressure in the interior volume of the cartridge from the pressure sensor;
obtain a second pressure reading of the pressure in the interior volume of the cartridge from the pressure sensor following an operation configured to deliver fluid from the cartridge to a patient;
compare the first pressure reading to the second pressure reading;
determine, from the comparison, of the first pressure reading to the second pressure reading, whether the distal section of the spool moved axially at time during the operation configured to deliver fluid from the cartridge to the patient when the distal section should have remained stationary;
selectively generate an occlusion alarm based on the comparison of the first pressure reading to the second pressure reading if it is determined that the distal section moved at the time it should have remained stationary.

2. An ambulatory infusion system, comprising:
a disposable infusion cartridge, the infusion cartridge including a collapsible reservoir for containing a fluid and a substantially rigid shell disposed over the collapsible reservoir and forming an interior volume between an outside surface of the collapsible reservoir and an inside surface of the shell, the disposable infusion cartridge further including a delivery mechanism having a spool slidingly disposed in a bore, the spool including a main section and a distal section axially displaceable relative to the main section with a collapsible volume formed between a seal on the main section and a seal on the distal section;
a pump device configured to selectively receive the infusion cartridge and cooperate with the infusion cartridge to deliver fluid from the reservoir to the patient, the pump device including a drive mechanism powered by a motor and selectively engageable with the spool to impart controlled axial movements to the spool to deliver fluid from the cartridge to the patient;

a pressure sensor located in one of the infusion cartridge and the pump, the pressure sensor in communication with the interior volume of the infusion cartridge; and a processor located in one of the infusion cartridge and the pump, wherein the processor is adapted to:

actuate the motor to deliver a portion of fluid contained in the collapsible volume;

obtain a first pressure reading of the pressure in the interior volume of the Cartridge from the pressure prior to actuating the motor;

obtain the a second pressure reading of the pressure in the interior volume of the cartridge from the pressure sensor after the motor is powered down following actuation;

compare the first pressure reading to the second pressure reading; and selectively generate an occlusion alarm based on the comparison of the first pressure reading to the second pressure reading if the second pressure reading is not the same as the first pressure reading.

3. The system of claim 2, wherein the first pressure reading is obtained immediately prior to actuating the motor and the second pressure reading is obtained immediately after the motor is powered down following actuation.

4. The system of claim 2, wherein the processor is further adapted to generate the occlusion alarm only if the second pressure reading is not the same as the first pressure reading and at least one previously obtained pressure reading.

5. The system of claim 2, wherein the second pressure reading is not the same as the first pressure reading if it is not within a predetermined threshold of the first pressure reading.

6. An ambulatory infusion system, comprising:

a disposable infusion cartridge the infusion cartridge including a collapsible reservoir for containing a fluid and a substantially rigid shell disposed over the collapsible reservoir and forming an interior volume between an outside surface of the collar reservoir and an inside surface of the shell, the disposable infusion cartridge further including a delivery mechanism having a spool slidingly disposed in a bore, the pool including a main section and a distal section axially displaceable relative to the main section with a collapsible volume formed between a seal on the main section and a seal on the distal section;

a pump device configured to selectively receive the infusion cartridge and cooperate with the infusion cartridge to deliver fluid from the reservoir to the patient, the pump device including a drive mechanism powered by a motor and selectively eneageable with the spool to impart controlled axial movements to the spool to deliver fluid from the cartridge to the patient;

a pressure sensor located in one of the infusion cartridge and the pump, the pressure sensor in communication with the interior volume of the infusion cartridge; and a processor located in one of the infusion cartridge and the pump, wherein the processor is adapted to:

actuate the motor to deliver all fluid contained in the collapsible volume to the patient;

obtain a first pressure reading of the pressure in the interior volume of the cartridge from the pressure sensor at a time prior to all of the fluid being delivered;

obtain a second pressure reading of the pressure in the interior volume of the cartridge from the pressure sensor at a time after all of the fluid has been delivered;

compare the first pressure reading to the second pressure reading; and selectively generate an occlusion alarm based on the comparison of the first pressure reading to the second pressure reading if the second pressure reading is the same as the first pressure reading.

7. The system claim 6, wherein the first pressure reading is obtained prior to delivering any of the fluid and the second pressure reading is obtained prior to subsequent actuation of the motor to deliver a subsequent amount of fluid that has been drawn from the collapsible reservoir into the bore.

8. The system of claim 6, wherein the first pressure reading is made during a first fluid deliver cycle and the second pressure reading is made during a subsequent fluid delivery cycle, and each reading is taken at a common point in the respective delivery cycle.

9. The system of claim 6, wherein the processor is further adapted to generate the occlusion alarm only if the second pressure reading is the same as the first pressure reading and at least one previously obtained pressure reading.

10. The system of claim 6, wherein the second pressure reading is not the same as the first pressure reading if it is not within a predetermined threshold of the first pressure reading.

11. An ambulatory infusion stem, comprising:

a disposable infusion cartridge, the infusion cartridge including a collapsible reservoir for containing a fluid and a substantially rigid shell disposed over the collapsible reservoir and forming an interior volume between an outside surface of the collapsible reservoir and in inside surface: of the shell, the infusion cartridge further defining a collapsible volume for receiving fluid from the collapsible reservoir;

a pump device including a motor and configured to selectively receive the infusion cartridge and cooperate with the infusion cartridge to deliver fluid from the reservoir into the collapsible volume and to the patient;

a pressure sensor located in one of the infusion cartridge and the pump, the pressure sensor in communication with the interior volume of the infusion cartridge; and a processor located in one of the infusion cartridge and the pump, wherein the processor is adapted to:

actuate the motor to deliver fluid contained in the collapsible volume to the patient;

obtain a first pressure reading of the pressure in the interior volume of the cartridge from the pressure sensor prior to actuating the motor;

cease actuation of the motor after delivering a desired amount of the fluid from the collapsible volume;

obtain a second pressure reading after ceasing actuation of the motor;

compare the first pressure reading to the second pressure reading; and generate an occlusion alarm if the second pressure reading is not the same as the first pressure reading.

12. The system of claim 11, wherein the first pressure reading is obtained immediately prior to actuating the motor and the second pressure reading is obtained immediately after ceasing actuation of the motor.

13. The system of claim 11, wherein the processor is further adapted to generate the occlusion alarm only if the second pressure reading is not the same as the first pressure reading and at least one previously obtained pressure reading.

14. The system of claim 11, wherein the second pressure reading is not the same as the first pressure reading if it is not within a predetermined threshold of the first pressure reading.

15. The system of claim 11, wherein the processor is adapted to deliver only a portion of the fluid in the collapsible volume between actuating the motor and ceasing actuation of the motor.

16. An ambulatory infusion system, comprising:
a disposable infusion cartridge, the infusion cartridge including:
   a collapsible reservoir for containing a fluid;
   a substantially rigid shell disposed over the collapsible reservoir and forming an interior volume between an outside surface of the collapsible reservoir and an inside surface of the shell; and
   a delivery mechanism having a spool slidingly disposed in bore, the spool including a main section and a distal section axially displaceable relative to the main section with a collapsible volume formed between a seal on the main section and a seal on the distal section;
a pump device configured to selectively receive the infusion cartridge, the pump device including a drive mechanism powered by a motor and selectively engageable with the spool to impart controlled axial movements of the spool to deliver fluid from the reservoir into the collapsible volume and to a patient; and
a processor located in one of the infusion cartridge aid the pump, wherein the processor is adapted to
   actuate ail operation to deliver fluid stored in the collapsible volume to the patient;
   determine whether the distal section of the spool moved axially at a time during the operation configured to deliver fluid from frond the reservoir to the patient when the distal section should have remained stationary; and
   generate an occlusion alarm if it is determined that the distil section moved at the time it should have remained stationary.

17. The system of claim 16, further comprising a pressure sensor located in one of the infusion cartridge and the pump, the pressure sensor in communication with the interior volume of the infusion cartridge and wherein the processor is further adapted to:
   obtain a first pressure reading of the pressure; in the interior volume of the cartridge from the pressure sensor;
   obtain a second pressure reading of the pressure in the interior volume of the cartridge from the pressure sensor following the operation configured to deliver fluid from the reservoir to a patient;
   compare the first pressure reading to the second pressure reading; and
   selectively generate the occlusion alarm based on the comparison.

18. The system of claim 17, wherein the processor is further adapted to determine that the distal section of the spool moved and generate the alarm if the second pressure reading is not the same as the first pressure reading.

* * * * *